United States Patent [19]

Umezawa, deceased et al.

[11] Patent Number: 5,202,427
[45] Date of Patent: Apr. 13, 1993

[54] DNA SEGMENT CONTAINING STREPTOMYCIN RESISTANCE GENE AND BEING CAPABLE OF CONTROLLING EXPRESSION OF SAID GENE

[75] Inventors: Hamao Umezawa, deceased, late of Tokyo, Japan, by Mieko Umezawa, legal representative; Yoji Umezawa, heir; Yoji Umezawa, heir; Yoshiro Okamo, heir, all of Tokyo, Japan

[73] Assignee: Zaidan Hojin Biseibutsu Kagaku Kenkyu Kai, Japan

[21] Appl. No.: 659,469

[22] Filed: Feb. 25, 1991

Related U.S. Application Data

[63] Continuation of Ser. No. 93,530, Jul. 20, 1987, abandoned.

[30] Foreign Application Priority Data

Nov. 20, 1985 [JP] Japan .............................. 60-258622

[51] Int. Cl.⁵ .................... C12N 15/52; C12N 15/31; C12N 15/00; C12N 15/74
[52] U.S. Cl. .................. 536/24.1; 435/172.3; 435/320.1; 435/252.35; 935/14; 536/23.2
[58] Field of Search ... 435/172.1, 172.3, 252.3–252.35, 435/193, 320.1; 536/27; 935/11, 14

[56] References Cited

PUBLICATIONS

Distler et al.; FEMS Microbiol. Lett. 28: 113 (1985).
Tohyama et al.; Chem. Abstr. 102: 73512c (1985).
Vallins et al.; J. gen. Microbiol. 131: 1657 (1985).

*Primary Examiner*—James Martinell
*Attorney, Agent, or Firm*—Larson and Taylor

[57] ABSTRACT

A DNA segment of this invention is a DNA fragment of a length of about 3.8 kb which is obtained by excising with a restriction endonuclease Bgl II a hybrid plasmid pST 141 having a length of about 12.6 kb of *Streptomyces griseus* 4-1 strain (FERM P-7984, namely, FERM BP-1198) to give a Bgl II-Bgl II DNA fragment, and then excising with a restriction endonuclease Sph I the resultant Bgl II-Bgl II DNA fragment having a length of about 7.0 kb and having the restriction endonuclease sites as shown in the restriction endonuclease map of FIG. 1. This DNA fragment is a DNA which contains a streptomycin resistance gene and contains, in the vicinity of this gene, such a DNA region possessing a function to control the expression of the streptomycin resistance gene. An insertion of this DNA fragment having a length of about 3.8 kb into a suitable actinomycetes plasmid vector can produce such a hybrid plasmid which acts reliably as a selected marker of the streptomycin resistance.

2 Claims, 7 Drawing Sheets

FIGURE 3 (Part 1)

SphI(3)
```
                                                             60
GCATGCACCGACTGCGCGCCACCAAAATGCGCGGAGCCACCGAGATCGCCGTGCGGTATT

120
TCGAAGGCGGAGAGGAAGAGGCGTTCATCTTCGCGGTGAAGTCCAACGTCACCCACGGAC

180
TGCCGCTCTCCCTCGACGACCGCAAGGCCGCGGCGACCCGTGTCCTGGAGACCCATCCGT

240
CCTGGTCCGACCGGGCCATCGGCCTGGCGACCGGACTGTCGGCGAAGACGGTGGGGACCC

300
TCAGGGTCCTGTTCGACTGCCGGGTTCCGCAGTCGAACGTGAGGATCGGGAGGGACGGGC

360
GGGCCCGGCCGCTGGACCCCACCGAGGGGCGGAAGCTGGCGAGCCGGCTGCTCCAGGAGA

420
ACCCCTCGGCGTCGCTGCGTCAGATCGCCGCACAGGCCGGCGTCTCCCCGAGCACCGCCT
```
AatII                                        HincII  480
```
CCGACGTCCGCAAGCGCTGAGCCGTGGTGAGAGCCCGCTGCCCGAACGCGATCGTCAACA
```
                                     SmaI       540
```
GGAAGTGCCGGCCGTCGCCCGGCACTCCGCCCGTGTCTCCCGGGCCGACGGGAGTTGGGC
     ——————————————→    ←——————————

600
GCCGCACACCGTGGCCGTGCGGCCACCTCAGCCGGGACCCGTCCGTGCGGCTCACCGAGG

660
ACGGTCGGGCGCTGCTACGTTGGCTGAACGTGGTGGCCGTGCGCAACCAGGACTGGGACC

720
GCCTCCTGGGCAACGTCCCTCCGCACTGCGTCAAGGTCATAGCCGAGCTGGCCCGTGGCT

780
GTGCCGACATCTGGCATCGGGTGGCGGAGGAACTGGACCAGGCCGGCATCGACGAGGCGG

840
CGGGCCGGTCCTTGAGCGATGTCGGATGACGGCGGGAGCCGCCCGCCCGCGACGGAGTTG
```

FIGURE 3 (Part 2)

```
                                                            900
AGGAGCGTCGGCCGTGCACCCGACGGGGGAGCGGTGCCGTCCCGCGGCAGCCGCCGGGCA

960
CTTCAGGCCGCCCGAAGCCGCCGTGCCCGAAGCACGTGAACCACTGCATCACGCAAGGCC

1020
GCGGCTTCGCCGACGGGCTCCGAGGGGGCGCGTCGGCGCGAGCCGCGGCGGCAGACCCAT
         ──────>                    <──────    ──────
             *1043                                         1080
CCCATGTGTAAGGAAATTTCCATGAGTTCGTCGGACCACATCCACGTCCCGGACGGCCT
     ──────>         <──────

1140
GGCCGAGTCGTACAGCAGAAGCGGTGGCGAGGAAGGGCGCGCCTGGATCGCCGGACTTCC

SalGI                                        1200
CGGCTCTCGTCGCGATCGTCGACCGCTGGGAGCTGAAGAGGGACGGCGGCGTCCGCTC (a) AatI (1)                                            1260
CGGTGAGGCCTCCCTCGTGGTGCCGGTGCTGCGTGCTGACGGCACGCGGGCGGCGCTCAA

SmaI                                          1320
ACTCCAGATGCCCCGGGAAGAGACGACGGCCGCGCTGATCGGCCTGCGAGCCTGGGGCGG

1380
GGACGGCATGGTGCGGCTGCTCGACCACGACGAGGAGAGCAGCACGATGCTGCTGGAACG

1440
CCTGGGACGGTTCGCGGACGTGGCGTCGGTCGAGGACGACGACGAGGCCATGGGCGTCCT

1500
CGCCGGGCTGCTGAACCGGCTGCACTCCGTTCCGGCACCTCCGGGGCTGCGGGGTCTGGG

SalGI    BamHI (4)1560
AGAGATCGCCGGCGCCATGGTGGAGGAAGTTCCCTCCGCTGTCGACTCGTTGGCGGATCC

1620
GGAGGACCGTAGCCGGTTGCGCGCCGTGGGCGTCGGCCGTGAGCCGCTGGTGGGCGAGCC

1680
CGGTGACCGCGTCCTGCACTGGGACCTGCACTACGAGAACGTGCTGGCCGCCGAGCGCGA
```

FIGURE 3 (Part 3)

```
                                              SmaI              1740
ACCGTGGCTGGCCATCGACCCCGAGCCGCTGGTCGCGGACCCGGGGTTCGACCTGTGGCC

1800
GGCCCTGGACACCGGTTGGGAGCGGATCGAGGCCACCGGTGACGCGCGGCGGGTGGTCCG

1860
GCGGCGCTTCGACCTGCTGACGGAAGCGCTGGAGCTGGACCGCGGGAGGGCGGCCGGGTG (c) PstI                                              1920
GACCCTGGCCCGGCTCCTGCAGAACACCCTGTGGGACATCGAGGACGGGCTGACGGCGAT

*1966            1980
CGCCCCCTCCCAGATCGCCGTGGCCGAAGCGCTGGCGAAGCCCTGAACTCCTGAAGCACT
                                              ─────────────────>
                                                                2040
GAAGCCCTGAAGCACGGAAGCGGGGGGCGGGCCGCCGACGGCCCGCGCCCCGCCGCACCT
─────────────>    ──────────────────────>    <──────────────────
                                                                2100
CCGATGCGTTCGACTGCCGATCACACGCAGTCGAACGCATCCGGCGTCCGCCGGCCGTGG
─────────────>              <────────────────
                                                                2160
GCCGCCGCGGTGGACATATGCCCGAGCGAAGCGGCGCTGCTAGCCTGCGATGAGTACGGG

2220
AGAGCAGGCGACCGGTGGACCACCGGGTTCACCCTTCGCCTCCCGCCCGTCGTGATCCCC (d) BamHI(3)       XhoI                               2280
CGCGTCCAGCGGATCCGCAGCACCCCCTCGAGTACCCGCCCGGCTCAGTCCGTGCACGCG

2340
TGTGTCCGCACCCGCCCCTGTACGCCGAGCACTGCCGAGTCGAGCCTTCGCGGCGGACCG
                                                        ────────
                                                                2400
CACCGGCTGCGCGGTCCGCGCTTCCGTCCGTGCCCGCCCGGCGAAGGACGGGGCCGCCGC
────────────<                                       ────────────>
                                                                2460
CGTGGTCCCGCGACCGTCCCGGCCGTCGTCATGCCCCACCTGATGGAGGAGAGTCATGAG
───────────                                    ────────
                                                                2520
CCTTGTAAGCGTCCACAACGAATGGGACCCGCTGGAGGAGGTCATCGTCGGCACGGCGGT
```

FIGURE 3 (Part 4)

```
      SmaI                                               2580
GGGCGCCCGGGTTCCCACCGCGGACCGAAGCGTCTTCGCGGTGGAGTACGCGGGGGACTA

2640
CGAGAGCCAGGAGCAGATCCCCTCGGGTGCCTACCCGGACCGTGTGCTCAAGGAGACCGA

HincII                    2700
AGAGGAACTCCACGTACTCGCGGCGGAGTTGACCAAGCTCGGAGTCACCGTCCGGCGCCC BclI                              2760
CGGCCCTCGCGACCACTCAGCCCTGATCAAGACCCCCGACTGGGAGACGGACGGGTTCCA

2820
CGACTACTGCCCGCGCGACGGCCTGCTGTCGGTGGGGCAGACCATCATCGAGACACCGAT

ScaI         2880
GGCCCTCCGGTCCCGCTTCCTGGAGTCGCTCGCCTACAAGGACCTCCTGCTGGAGTACTT (e) BamHI(2)                                         2940
CGCCGAGCGGATCCGCTGGCTGTCCGCGCCCAAGCCGCGGCTGACCGACGACTCCTACGC

3000
CCCGCAGGCCCCGGCCGGCGAGCGCCTCACCGACGAGGAGCCGGTGTTCGACGCCGCCAA

3060
CGTGCTGCGCTTCGGCACCGACCTGCTCTACCTGGTGTCGGACAGCGGCAACGAACTGGG

3120
CGCCAAGTGGCTCCAGTCGGCGGTCGGCGACACCTACACCGTCCACCCCTGCCGCAAGCT

SalGI                                          3180
GTACGCCTCCACCCACGTCGACTCCACCATCGTGCCCCTGCGGCCCGGCCTCGTCCTGAC

3240
CAACCCCTCACGGGTGAACGACGAGAACATGCCCGACTTCCTGCGGTCCTGGGAGAACAT (f) SstI                                            3300
CACCTGCCCCGAGCTCGTGGACATCGGCTTCACCGGCGACAAGCCGCACTGCTCGGTGTG

SalGI        3360
GATCGGGATGAACCTGCTGGTGGTGCGGCCCGACCTGGCCGTGGTCGACCGCCGGCAGAC
```

FIGURE 3 (Part 5)

```
                                                   (g) PvuII 3420
CGCGCTGATCCGGCTTCTGGAGAAGCACGGCATGAACGTGCTGCCCCTCCAGCTGACCCA

3480
CTCGCGCACCCTCGGGGGGCGCTTCCACTGCGCGACCCTCGACGTGCGGCGACGGCCGCT

3540
GGAGACGTACCAGTTCTGAGAGCGACCACTCAACTCCGTTACGGCTAGGGAGGTTGTCAC

3600
AGTGATTGGCTACGGCGTCTGCGTCGGCCCCGGCACCCTGTTCGAGCGCACGTGTCTGCC

3660
GGGCATCGAGCGCGTCCGGGCACCGGGCAGCCCGGTGTTCACCATGCGCAACCAGCGTTC
───→      ──────────────→  ←──────────
                                                             3720
GCTGTTCTCCGCCTACAACGCCATGTTCGACCAGGCGGCCGCGAACTCGGACATCACCGG

3780
CCTGGTGATGCTCCACGACGACGTCGSGTTGCGGAAGAACCCCGCCGAGGTGGCGCAGTC (h) SphI(2)           (i) BamHI(1) 3830
CGTCTTCGAGGACGATTCCGTGGGCATGCTCGGCTCGGTCGGCGGGATCC
```

DNA SEGMENT CONTAINING STREPTOMYCIN RESISTANCE GENE AND BEING CAPABLE OF CONTROLLING EXPRESSION OF SAID GENE

This application is a continuation of application Ser. No. 07/093,530 filed Jul. 20, 1987, now abandoned.

TECHNICAL FIELD

This invention relates to a DNA segment containing a streptomycin resistance gene of an actinomycetes and possessing a function to control the expression of said gene. Particularly, this invention is concerned with a novel DNA segment containing a streptomycin resistance gene for encoding a streptomycin-inactivating enzyme (streptomycin phosphotransferase) and also containing a DNA region possessing the function to control the expression of said gene.

BACKGROUND ART

Actinomycetes are important microorganisms which have found wide-spread utility in the microbiological industry, as microorganisms for producing the useful substances such as antibiotics.

It is extremely beneficial from the industrial standpoint to use the recombinant DNA technology for the breeding of actinomycetes or for the elucidation of the genetic characteristics of actinomycetes.

From such a viewpoint, many plasmid vectors which are usable for actinomycetes have been constructed and reported. It has however been found that when a gene of actinomycetes is inserted in these known plasmid vectors, the gene thus inserted is not always expressed as desired and the expression of the gene is not affected by any artificial control. The conventional actinomycetes plasmid vectors were, therefore, not fully satisfactory for such a genetic engineering procedure which requires a skill of high order for the control of the expression of genes.

The present inventors have made investigations in an attempt to make improvements in these problems. As a result, we have now succeeded in isolating such a novel DNA fragment which contains the streptomycin resistance microorganism, *Streptomyces griseus* ISP 5236 (ATCC gene of a 23345), a known streptomycin-producing strain, and which also contains a DNA region possessing a function to control the expression of said gene. It has also been found that even when the streptomycin resistance gene is introduced into a plasmid vector with omitting the DNA region which possesses the function to control the expression of the streptomycin resistance gene, in the resulting plasmid vector recombinant DNA molecule, the streptomycin resistance gene introduced is not expressed as desired.

The present inventors have already attempted the isolation of the streptomycin resistance gene from the above-mentioned *Streptomyces griseus* ISP 5236 known as the streptomycin-producing microorganism, as well as the cloning of said gene. As a result of the experiments, the location and characteristics of the streptomycin resistance gene were elucidated to some extent (Japanese Patent Application No. 265373/79 filed Dec. 18, 1979; see Japanese Patent Application first publication "Kokai" No. 146186/86).

Thus, the streptomycin resistance gene has already been found by the present inventors to have the following characteristics:

(a) The gene is comprised in a Bgl II-Bgl II DNA fragment of a length of about 7.0 kilobose (kb) which is obtained by cutting or excising the DNA of the chromosome which governs the streptomycin resistance of *Streptomyces griseus*, with a restriction endonuclease Bgl II.

(b) The restriction endonuclease map of the above DNA fragment of a length of about 7.0 kb, which contains said gene, is as shown in FIG. 1 of the accompanying drawings.

(c) The gene encodes a phosphotransferase, the enzyme which phosphorylates the 6-OH group of an aminoglycoside antibiotic, notably, streptomycin.

The present inventors have also found that the above streptomycin resistance gene locates in such a DNA fragment which is obtained by cleaving with a restriction endonuclease Sph I, the above-mentioned Bgl II-Bgl II DNA fragment of about 7.0 kb in length, which had, in turn, been obtained by excising the chromosome DNA of *Streptomyces griseus* with the restriction endonuclease Bgl II (see Japanese Patent Application first publication "Kokai" No. 146186/86 referred to above).

Further, the present inventors also have succeeded in constructing a novel hybrid plasmid by insertion of said Bgl II-Bgl II DNA fragment of a length of about 7.0 kb which contains the streptomycin resistance gene ("streptomycin" is hereinafter abbreviated as "SM"), into the restriction endonuclease Bgl II-cleavage site of the DNA of a known plasmid pIJ 702, in accordance with a known gene recombination technique. This novel hybrid plasmid was named "pST 141". It was also found that the plasmid pST 141 has a length of about 12.6 kb, and the restriction endonuclease map of this hybrid plasmid pST 141 is as illustrated in FIG. 2 of the accompanying drawings (see the above-mentioned Japanese Patent Application first publication "Kokai"). A *Streptomyces lividans* transformant containing the plasmid pST 141 has been deposited under FERM P-7984 since Dec. 6, 1984 with "Fermentation Research Institute, Agency of Industrial Science of Technology" located at No. 1-3 Higashi 1-chome, Yatabe-machi Tsukuba-shi, Ibarakiken, Japen (305), and it has also been deposited there under FERM BP-1198 through the procedure of transfer which was done in accordance with the provisions of the International Deposit prescribed in the Budapest Treaty.

An invention was thus completed and claimed in Japanese Patent Application No. 265373/79, which relates to "A DNA segment containing a streptomycin resistance gene therein, characterized in that said segment is equivalent to such a DNA fragment which has been originated from the DNA of *Streptomyces griseus* and which is located in a hybrid plasmid pST 141; said hybrid plasmid pST 141 being a hybrid plasmid composed of a Bgl II fragment of the DNA of *Streptomyces griseus* and of a Bgl II fragment of the DNA of a plasmid pIJ 702; and said plasmid pST 141 having the restriction endonuclease cleavage sites shown in FIG. 2 of the accompanying drawings and also having a length of about 12.6 kb".

The present inventors have now proceeded with a further investigation. Thus, the above-described Bgl II-Bgl II DNA fragment which has been obtained by excising the DNA of the chromosome of *Streptomyces griseus* with the enzyme Bgl II, has the restriction endonuclease map of FIG. 1, contains the SM resistance gene and has a length of about 7.0 kb is now further excised with a restriction endonuclease Sph I to give a Sph I-Sph I fragment. The resulting Sph I-Sph I fragment is then excised with a restriction endonuclease Pst I to give a Sph I-Pst I fragment, or the resulting Sph I-Sph I fragment is then excised with a restriction endonuclease Bam HI to give a Sph I-Bam HI fragment. The Sph I-Pst I fragment and the Sph I-Bam HI fragment so obtained are used separately and inserted into various vectors so that various types of plasmids are reconstructed. The various types of plasmids thus obtained are then introduced separately into cells of such a strain of Streptomyces lividans which intrinsically does not produce streptomycin. Various kinds of the resultant transformants of Streptomyces lividans are separately cultured. Streptomycin is added to the culture broth of the respective transformants, followed by further incubation. From the states of growth of the individual transformants in the incubation experiments, it is examined whether or not a streptomycin-inactivating enzyme is produced by the individual transformants. Further, it is also investigated from the results of the above examination whether or not the SM resistance gene present in the plasmids as introduced is expressed. As a result of the above investigations, it has been found that such strains which do not or little show the expression of the SM resistance gene are occurring, in addition to the strains which show the SM resistance, even when the so incubated strains are such those that have been transformed just by the plasmids containing the entire DNA sequence which is corresponding to the SM resistance gene. With the foregoing in view, a further investigation has been continued. As a result, it has now been found that the above-described Sph I DNA fragment of a length of about 3.8 kb, which is obtained by excising with the enzyme Sph I the aforementioned Bgl II-Bgl II fragment of a length of about 7.0 kb having the restriction endonuclease map of FIG. 1 and containing the SM resistance gene, does contain such DNA region which possesses the function to control the expression of the SM resistance gene, namely, such a DNA region which is capable of sensing the existence of streptomycin as added artificially from the outside and capable of governing, i.e., controlling the expression of the SM resistance gene and also that the SM resistance gene is not expressed as desired unless the DNA region possessing the function to control the expression of the gene is existing in the vicinity of the SM resistance gene. Some part of these finding have already been reported by the present inventors in "The Journal of Antibiotics", Vol. 39, No. 10, 1505-1507 (published Oct. 25, 1986).

The present inventors have hence expected that a recombinant plasmid capable of reliably acting as a selected marker of the SM resistance is possible to be constructed by inserting into a plasmid vector said SM resistance gene, in association with such DNA fragment consisting of the above-mentioned DNA region which possesses the function to control the expression of the SM resistance gene, or a DNA fragment comprising said DNA region, in case such DNA fragment can be isolated and recovered. Moreover, such a host strain as transformed by the recombinant plasmid which contains the SM resistance gene as well as the DNA fragment (region) possessing the function to control the expression of the SM resistance gene will be able to show the expression of the SM resistance gene as desired artificially when a substance capable of inducing the expression of the SM resistance gene, for example, streptomycin is added externally. It is also expected that when the above-mentioned DNA fragment (or region) possessing the function to control the SM resistance gene, as well as an appropriate gene in place of the SM resistance gene are inserted into a plasmid according to a DNA recombinant technique and when the recombinant plasmid so obtained is introduced into a host cell of actinomycetes, said appropriate gene is possible to be expressed as desired in the transformant of the host actinomycetes cell. Therefore, the DNA fragment having the function as above described is industrially useful in various aspects. The present inventors have now succeeded in obtaining such a novel DNA fragment.

DISCLOSURE OF THE INVENTION

The subject of this invention therefore resides in a DNA segment containing a streptomycin resistance gene and possessing a function to control the expression of the gene, characterized in that said DNA segment is an Sph I-Sph I DNA segment which is obtained by excising a Bgl II-Bgl II fragment with a restriction endonuclease Sph I, said Bgl II-Bgl II fragment having been obtained by excising a hybrid plasmid pST 141 with a restriction endonuclease Bgl II, and said Bgl II-Bgl II fragment having been derived from the DNA of Streptomyces griseus and containing the streptomycin resistance gene therein and having the restriction endonuclease sites shown in the restriction endonuclease map of FIG. 1 of the accompanying drawings and a length of 7.0 kb., and said hybrid plasmid pST 141 having been constructed by ligating a Bgl II fragment of the DNA of a plasmid pIJ 702 with such a Bgl II fragment of a length of 7.0 kb which is obtained by excising with the restriction endonuclease Bgl II the chromosome DNA containing the streptomycin resistance gene of Streptomyces griseus; and said hybrid plasmid pST 141 also having the restriction endonuclease cleavage sites shown in the restriction endonuclease map of FIG. 2 of the accompanying drawings and having a length of about 12.6 kb, and that said DNA segment is such DNA segment having a length of about 3.8 kb and containing internally the streptomycin resistance gene and a DNA region possessing the function to control the expression of the streptomycin resistance gene, or a DNA segment which is equivalent to the first mentioned DNA segment.

BRIEF DESCRIPTION OF THE DRAWINGS

FIG. 3 (parts 1-5) is shows a diagram of the sequence of DNA bases (nucleotide) of such region which is a portion extending from the Sph I(3) site to the Bam HI(1) site (having a length of about 3.8 kb) present in the DNA fragment of the 7.0 kb length as depicted on the restriction endonuclease cleavage map of FIG. 1 and which contains the streptomycin resistance gene.

Figure 1:
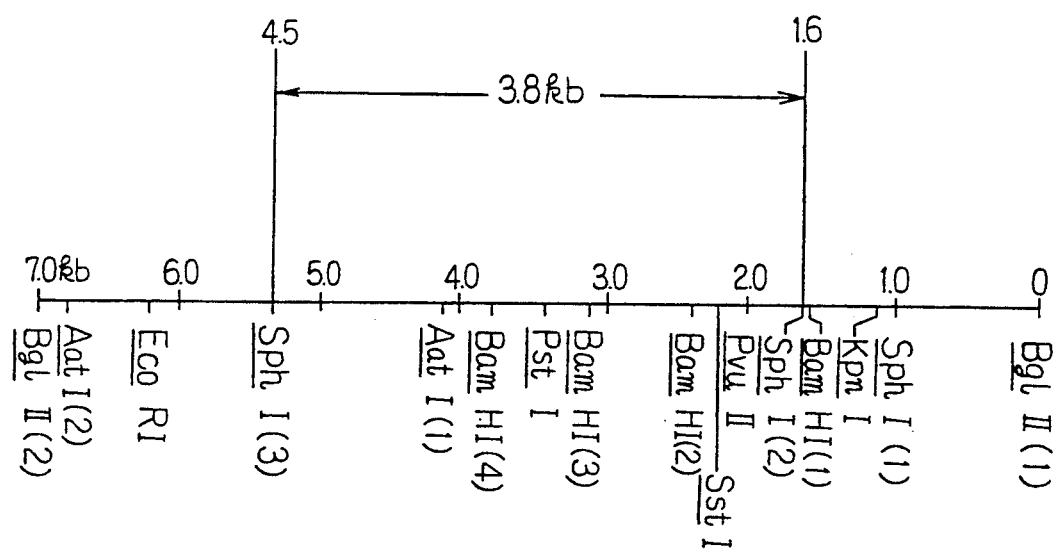
FIG. 1 shows a restriction endonuclease cleavage map of a DNA fragment of a length of 7.0 kb which is obtained by excising the chromosome DNA of Streptomyces griseus with the restriction endonuclease Bgl II and which contains the streptomycin resistance gene.

The novel DNA segment above described according to this invention is present specifically in a DNA fragment of a length of about 3.8 kb which is obtained when such a Bgl II fragment of a length of 7.0 kb which has been obtained by cutting the chromosome DNA of a streptomycin-resistance strain of Streptomyces griseus with the restriction endonuclease Bgl II and which is depicted by the restriction endonuclease cleavage map as shown in FIG. 1, is further excised at the Sph I(2) cleavage site and at the Sph I(3) cleavage site appearing in FIG. 1.

Incidentally, in this invention, by a DNA segment "which is equivalent to such DNA segment containing internally the streptomycin resistance gene and a DNA region possessing a function to control the expression of said gene" is meant not only such a DNA segment which has exactly the same base (nucleotide) sequence as the aforesaid DNA segment, but also such a DNA segment which has a different base (nucleotide) sequence due to degeneracy of the DNA codons but retains the same function as that of the aforesaid DNA segment.

BEST MODE FOR WORKING THE INVENTION

Figure 2:
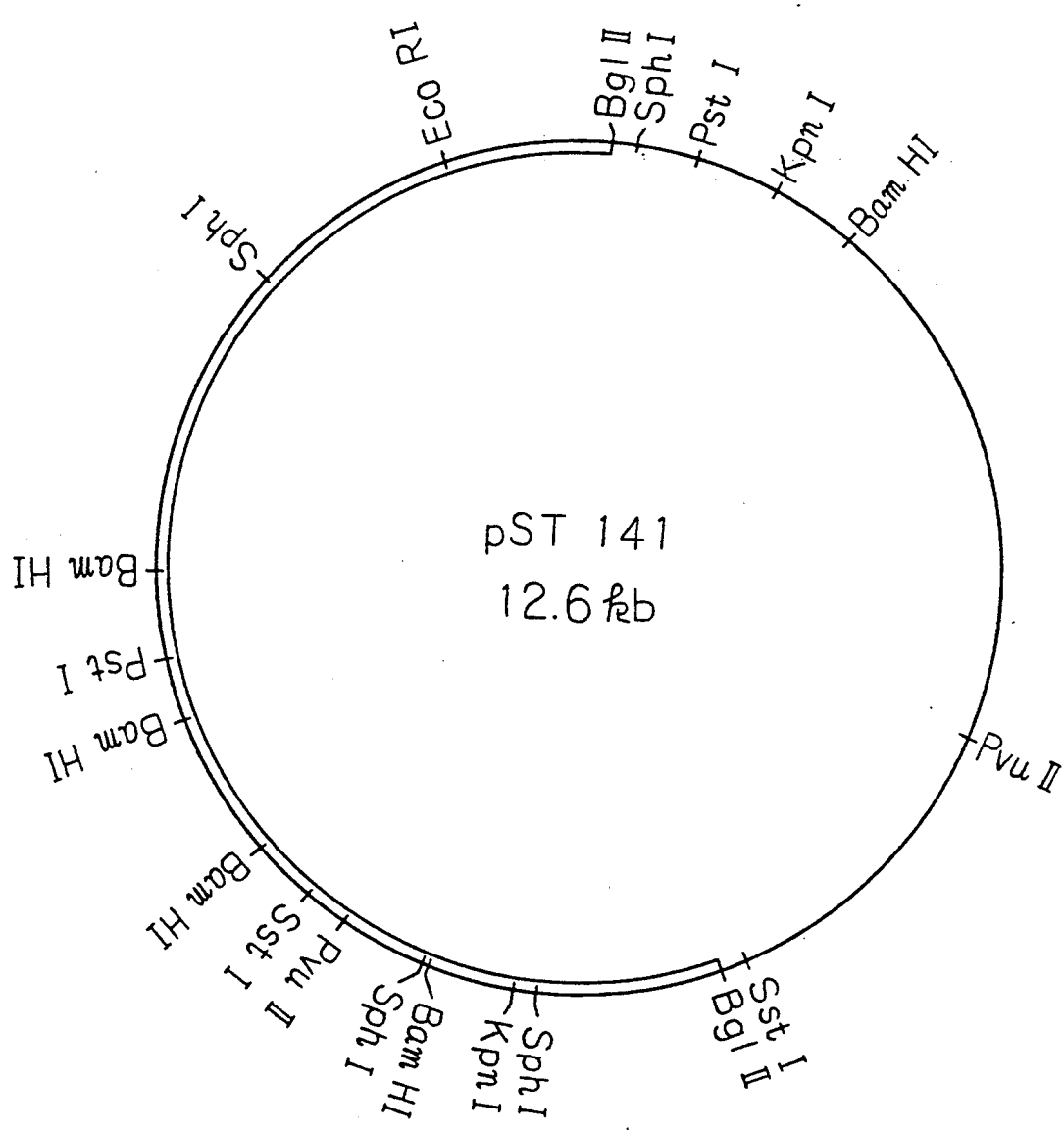
FIG. 2 shows a restriction endonuclease cleavage map of a hybrid plasmid pST 141 which has been constructed by insertion of the DNA fragment of FIG. 1 into a plasmid vector pIJ 702.

One specific example of the novel DNA segment according to this invention may be obtained as a DNA segment of a length of about 3.8 kb, by isolating from a host cell of actinomycetes the hybrid plasmid pST 141 (which has a restriction endonuclease map as shown in FIG. 2 and a length of about 12.6 kb and which had been already constructed by the present inventors), then excising the plasmid pST 141 with the restriction endonuclease Bgl II and further excising the resulting Bgl II-Bgl II DNA fragment (which has a length of about 7.0 kb and has been derived from *Streptomyces griseus* and which has a restriction endonuclease map as shown in FIG. 1) with the restriction endonuclease Sph I at the cleavage sites Sph I(2) and Sph I(3) appearring in FIG. 1.

An analysis has now been completed on the sequence of the bases (nucleotides) in such a DNA fragment having a overall length of 3830 bases, which extends from one Sph I cleavage site [the cleavage site as indicated by the letters Sph I(3) in FIG. 1]present at the upstream side of the above-described DNA segment of about 3.8 kb length, beyond the second Sph I cleavage site [the cleavage site as indicated by the letters Sph I(2) in FIG. 1]as seen in the sense of from the upstream to the downstream of the DNA segment, to the cleavage site as indicated by the letters Bam HI(1) in FIG. 1. This base (nucleotide) sequence as analyzed is shown in FIG. 3 of the accompanying drawings. In the base sequence of FIG. 3, the GCATGC region as indicated by the letters Sph I(3) given thereabove at the leading end of the base sequence of FIG. 3 is corresponding to the Sph I(3) cleavage site shown in the map of FIG. 1. Further, the AGGCCT region as indicated by the letters (a)Aat I(1) given thereabove is corresponding to the Aat I(1) cleavage site shown in FIG. 1. The GGATCC region as indicated by the letters Bam HI(4) and a line given thereabove corresponds to the Bam HI(4) cleavage site shown in FIG. 1. The CTGCAG region as indicated by the letters (c)Pst I given thereabove corresponds to the Pst I cleavage site in FIG. 1, the GGATCC region as indicated by the letters (d)Bam HI(3) given thereabove corresponds to the Bam HI(3) cleavage site in FIG. 1, the GGATCC region as indicated by the letters (e)Bam HI(2) given thereabove corresponds to the Bam HI(2) cleavage site in FIG. 1, the GAGCTC region as indicated by the letters (f)Sst I given thereabove corresponds to the Sst I cleavage site in FIG. 1, the GAGCTG as indicated by the letters (g) Pvu II given thereabove corresponds to the Pvu II cleavage site in FIG. 1, the GCATGC region ranging from the 3804th G to the 3809th C and as indicated by the letters (h)Sph I(2) given above corresponds to the Sph I(2) cleavage site in FIG. 1, and the GGATCC region ranging from the 3825th G to 3830th C and as indicated by the letters (i)Bam HI(1) given thereabove corresponds to the Bam HI(1) cleavage site in FIG. 1. It has now been determined that the DNA fragment extending from the 1043rd A to the 1966th A in the base sequence shown in FIG. 3 constitutes the streptomycin resistance gene as described above.

The DNA segment of this invention can hence be said to be either a DNA segment having the nucleotide sequence which appears in FIG. 3 of the accompanying drawings, and which extends from the DNA region corresponding to the Sph I cleavage site as indicated by the letters Sph I(3) given thereabove, to the DNA region corresponding to the Sph I cleavage site as indicated by the letters Sph I(2) given thereabove, when observed with reference to the DNA base (nucleotide) sequence diagram as shown in FIG. 3 of the accompanying drawings, or a DNA segment which is equivalent to the aforesaid DNA segment by virtue of a degeneracy of codons.

The production of the novel DNA segment of this invention can be performed by an artificial synthesis, since the nucleotide sequence of the DNA segment has been revealed as described above. On the other hand, it is also possible to produce the novel DNA segment directly from the DNA of *Streptomyces griseus* or its variant, by using a general gene recombination technique. However, it is convenient to obtain the novel DNA segment by excising or cutting with restriction endonuclease the plasmid pST 141 of the strain, *Streptomyces lividans* 4-1 (see Japanese Patent Application first publication "Kokai" No. 14686/86), which has been deposited under FERM BP-1198 with "Fermentation Research Institute, Agency of Industrial Science and Technology" (FERM). Thus, the plasmid pST 141 is obtained from *Streptomyces lividans* 4-1 by a routine gene recombination technique. This plasmid is then excised by the restriction endonuclease Bgl II, followed by further excising with the restriction endonuclease Sph I to produce a mixture of DNA fragments of various lengths. The DNA fragment of a length of about 3.8 kb is then isolated from the above mixture by electrophoresis in agarose gel. The desired DNA segment of this invention can further be separated from the above fragment of about 3.8 kb.

Use of the DNA segment according to this invention can create such a novel recombinant DNA molecule which is constructed by inserting the DNA segment capable of encoding the phosphotransferase for inactivating streptomycin, namely, the above-described DNA segment (i) of this invention having a length of about 3.8 kb and containing the streptomycin resistance gene as well as the DNA region possessing the function to control the expression of the streptomycin resistance gene, into a suitable plasmid vector (ii), and which the novel recombinant DNA molecule, when introduced into a cell of suitable actinomycetes as a host, shows the ability to produce the streptomycin-inactivating phosphotransferase upon its detection of the existence of streptomycin. As a plasmid vector suitable for this purpose may be used the above-described plasmid pIJ 702. The Bgl II(1)-Sph I(1) fragment (length: 1.0 kb) which is present at the downstream side of the 7.0 kb DNA fragment as shown in FIG. 1 may be ligated to the Sph I cleavage site (the site as indicated by the letters Sph I(2) in FIG. 1) in the downstream side of the above-described DNA segment of this invention having the length of about 3.8 kb, to produce a recombinant DNA segment. By inserting this recombinant DNA segment into the Bgl II-Sph I cleavage site of the plasmid vector pIJ 702, a hybrid plasmid (recombinant DNA molecule) can be obtained. When this hybrid plasmid so obtained is further introduced into *Streptomyces lividans*, this hybrid plasmid can then detect the existence of streptomycin as added and can produce the phosphotransferase for inactivating streptomycin.

The present invention will next be described by Referential Examples and Experimental Examples.

REFERENTIAL EXAMPLE 1

(1) Cloning of SM-resistance DNA Segment Containing the SM Resistance Gene (a) Formation of Hybrid Plasmid

*Streptomyces griseus* ISP 5236 (ATCC 23345) was cultured at 27° C. for 2 days in 100 ml of a culture medium comprising 1% glucose, 0.3% yeast extract (Difco), 0.5% peptone (Difco) and 0.3% malt extract (Oxoid) which had been placed separately in 500 ml conical flasks. The culture broth obtained was centrifuged at 9000 rpm for 10 minutes to collect the cells.

After washing the cells with 2×TES buffer (comprising 50 mM Tris-HCl (pH 7.4), 50 mM EDTA and 50 mM NaCl), the cells were disrupted. From the cell homoginate as obtained, the chromosome DNA was extracted by a known method [the method of Carter et al., "Current Topics in Microbiology and Immunology" 96, 69(1981)]to obtain a donor DNA.

A 8 μg portion of the donor DNA thus obtained and 4 μg of the vector plasmid pIJ 702 of an actinomycetes were mixed together. Twenty units of the restriction endonuclease Bgl II were added to the resulting mixture, followed by effecting the cleavage reaction of the DNA at 37° C. for 1.5 hours in 50 μl of a buffer solution comprising 10 mM Tris-HCl (pH 7.5), 7 mM MgCl$_2$, 100 mM NaCl and 7 mM mercaptoethanol. After the cleavage reaction, the reaction mixture was heated at 68° C. for 10 minutes to inactivate the restriction endonuclease.

The resultant reaction solution containing the DNA fragments was admixed with the same amount of a phenol solution which had been saturated with a buffer solution comprising 0.1 M Tris-HCl (pH 8.0) and 0.2% mercaptoethanol, followed by shaking the resultant mixture. Then the whole mixture was centrifuged at 15,000 rpm for 1 minute. The aqueous layer was extracted twice with ethyl ether to remove the phenol. The aqueous layer was then mixed with a two-folds volume of chilled ethanol, and the resultant mixture was allowed to stand overnight at −20° C. Thereafter, it was centrifuged at 15,000 rpm for 10 minutes to recover the DNA fragments as a precipitate.

The DNA fragments thus recovered were dried under reduced pressure, followed by dissolution in 40 μl of purified water. To the resulting solution of the DNA fragments were added 5 μl of a buffer solution comprising 0.66 M Tris-HCl (pH 7.6), 66 mM MgCl$_2$, 0.1 M dithiothreitol and 10 mM ATP, and 15 units (5 μl) of T4-DNA ligase, followed by effecting the ligation reaction overnight at 4° C. In this way, there was obtained a mixture of various kinds of hybrid plasmids, including the hybrid plasmid pST 141 (having a length of about 12.6 kb) which was composed of the Bgl II-Bgl II DNA fragment (having a length of about 7.0 kb) of the chromosome DNA of *Streptomyces griseus* ISP 5236 as connected with the Bgl II fragment of the actinomycetes plasmid pIJ 702.

(b) Cloning

The mixture of various hybrid plasmids obtained in the above way was used to transform the protoplast of *Streptomyces lividans* 66 [J. Virology, 9, 258 (1972)] as a host. The SM resistance recombinant strains were selected from the resulting transformed cells. The hybrid plasmid pST 141 was further isolated from the cells of the SM resistant recombinant strains so obtained. The cloning of the SM resistance DNA segment containing the SM resistance gene therein was thus conducted in the above manner.

In the above case, the preparation of the protoplast of *Streptomyces lividans* 66 was carried out in the following manner. *Streptomyces lividans* 66 was inoculated in a culture medium comprising 1% glucose, 0.3% yeast extract (Difco), 0.5% peptone (Difco), 0.3% malt extract (Oxoid), 34% sucrose, 0.005 M MgCl$_2$ and 0.5% glycine, and then cultured for 2 days. The culture broth obtained was then subjected to centrifugation at 9,000 rpm for 10 minutes to collect the cells. The cells were washed with a solution of 10.3% sucrose. The cells washed were suspended in 16 ml of the P medium (comprising 10.3% sucrose, 0.025% K$_2$SO$_4$, 0.2% MgCl$_2$.2H$_2$O, 0.000008% ZnCl$_2$, 0.00004% FeCl$_3$.6H$_2$O, 0.000002% CuCl$_2$, 0.000002% MnCl$_2$.4H$_2$O, 0.000002% Na$_2$B$_4$O$_7$.10H$_2$O, 0.000002% (NH$_4$)$_6$Mo$_7$O$_{24}$.4H$_2$O, 0.005% KH$_2$PO$_4$, 0.37% CaCl$_2$.2H$_2$O and 25 mM TES buffer, pH 7.2) which further contained 1 mg/ml of egg white lysozyme. The resulting suspension was incubated at 32° C. for 60–90 minutes to form the protoplasts. The suspension was passed through a cotton filter and a 3.0 μm pore size filter, to remove such cells which had not been converted into protoplasts. The protoplasts were collected by centrifugation at 2,500 rpm for 10 minutes. After washing the collected protoplasts once with a volume of the P medium, they were suspended again in a further volume of the P medium at a concentration of 10$^9$–10$^{10}$ protoplast cells/ml.

To the above protoplast suspension was added 50 μl of the solution of the above-describe mixture of the hybrid plasmids containing the hybrid plasmid pST 141 which consisted of the Bgl II DNA fragments of the actinomycetes plasmid pIJ 702 and the Bgl II-Bgl II DNA fragment of the DNA of *Streptomyces griseus* ISP 5236. Immediately after the addition, a solution of polyethylene glycol #1000 (comprising a volume of the P medium containing 33% of polyethylene glycol #1000) was further added, and the resulting mixture was stirred for 60 seconds.

The mixture thus obtained was then diluted with 5 ml of the P medium, followed by centrifugation at 2,500 rpm for 10 minutes to collect the protoplasts.

The protoplasts so collected were suspended in 1 ml of the P medium, and the resultant protoplast suspension was applied in 0.1 ml portions as a coating layer onto a medium [comprising 10.3% sucrose, 0.025% K$_2$SO$_4$, 1% MgCl$_2$.6H$_2$O, 1% glucose, 0.01% Casamino acid (Difco), 0.000008% ZnCl$_2$, 0.00004% FeCl$_3$.6H$_2$O, 0.000002% CuCl$_2$, 0.000002% MnCl$_2$.4H$_2$O, 0.000002% Na$_2$B$_4$O$_7$.10H$_2$O, 0.000002% (NH$_4$)$_6$Mo$_7$O$_{24}$.4H$_2$O, 0.005% KH$_2$PO$_4$, 0.3% CaCl$_2$.2H$_2$O, 0.3% L-proline, 25 mM TES buffer (pH 7.2), 0.005 M NaOH and 0.5% yeast extract (Difco)], which had been charged separately and solidified in Petri dishes of 9 cm diameter and made of a plastic resin. The protoplasts were then incubated overnight at 27° C. On the incubated protoplasts was overlayed a soft agar medium of the same composition but containing 100 μg/ml of thiopeptin, in a volume of 1/4. The incubation was continued for additional 4 days to regenerate the protoplasts.

The regenerated clones were transferred to the ISP No. 4 medium, the ISP No. 4 medium containing 20 μg/ml of SM and the ISP No. 4 medium containing 50 μg/ml of SM, respectively, by the replica plating technique. The clones were cultured at 27° C. for 3 days. Such SM resistance clones which were grown concurrently in the SM-containing media and also in the SM-free medium were selected and taken.

From the cells of the SM resistance clones thus obtained, plasmids were extracted by the known method [Chater et al. "Current Topics in Microbiology and Immunology" 96, 69 (1981)]. Further, the SM resistance hybrid plasmid pST 141 of a length of about 12.6 kb in a purified form was isolated from the extracted plasmids.

(c) Assay

The SM resistance hybrid plasmid pST 141 so obtained from the SM resistance clones in the above manner were again excised by the restriction endonuclease Bgl II and then analyzed by electrophoresis in 0.7% agarose. By this analysis, the plasmid pIJ 702 employed as the vector as well as the DNA fragment of the length of about 7.0 kb were detected. Incidentally, when *Streptomyces lividans* 66 was transformed again in accordance with the above transformation method by introducing thereinto the hybrid plasmid pST 141 which had been obtained in the above cloning process, an SM resistance clone, namely, *Streptomyces lividans* 4-1 was produced again.

(2) Genetic Analysis

*Streptomyces lividans* 4-1 which had been transformed by the plasmid pST 141 as above was inoculated to a culture medium comprising 1% glucose, 0.3% yeast extract (Difco), 0.5% peptone (Difco) and 0.3% malt extract (Oxoid) and further containing 5 μg/ml of SM and was then cultured at 27° C. for 4 days. The resultant cells were collected by centrifugation of the culture broth at 9,000 rpm for 10 minutes and then washed with physiological saline. Thereafter, 10 g of the cells was suspended in 40 ml of a buffer solution comprising 125 mM Tris-malate and 12.5 mM MgSO$_4$ (pH 7.0). While being cooled in ice water, the cells were disrupted by sonification. The cell homoginate so disrupted was subjected to centrifugation at 16,000 rpm for 30 minutes, to obtain a cell-free enzyme extract.

The cell-free enzyme extract was added with 600 mg of ATP, 1 ml of toluene and 200 mg of streptomycin and incubated at 37° C. for 16 hours.

After the reaction mixture obtained was centrifuged at 16,000 rpm for 10 minutes the supernatant obtained was subjected to chromatography in a column of 100 ml of CM-Sephadex C-25 (which had been equilibrated with 0.1 M NaCl). After washing the column with water, the column was eluted with 0.1 M–1 M NaCl. Fractions of the eluate which were positive to the Sakaguchi reaction were collected and passed through a column of 50 ml of activated carbon. After washing this column with water, with 40% acetone and with 80% acetone, the column was eluted with 80% acetone containing 0.04 N HCl. Fractions of the eluate positive to the Sakaguchi reaction were collected, concentrated under reduced pressure and lyophilized to afford 103 mg of a powder. 50 mg of the powder was chromatographed in a column of 100 ml of Diaion LH-20 as a resinous adsorbent, followed by development with a mixture of methanol and water (1:1). Fractions of the eluate which were positive to the Sakaguchi reaction were collected, concentrated under reduced pressure and lyophilized to yield 20.9 mg of a powder.

This powder was analyzed with SIMS and $^{13}$C-NMR. A molecular ion peak was observed at 662, and it was confirmed that the powder was a streptomycin which had been phosphorylated at the 6-position.

It has thus been found that the SM resistance DNA segment of the length of about 7.0 kb as obtained in the above-described manner by cloning it from the SM resistance strain of *Streptomyces griseus* is able to encode the phosphotransferase (APH (6)) which phospharylates and inactivates the 6-OH group of streptomycin.

Experimental Example 1

In this Example, preparation of various kinds of deficient plasmids was conducted as follows:

(a) 1 μg of the plasmid pST 141 which was obtained from *Streptomyces lividans* 4-1 by the procedure (1)(b) of Referential Example 1 above was completely digested with the restriction endonuclease Sph I. The DNA ligase T4 was then added to the resultant digested mixture of plasmid fragments, followed by effecting the ligation reaction overnight at 4° C. The mixture of DNA segments of the various plasmid so ligated and reconstructed was used to transform protoplasts of *Streptomyces lividans* 66. The plotoplasts thus transformed were cultured and regenerated at 28° C. for 3 days in the R2YE medium which contained 20 μg/ml of thiopeptin. The clones thus regenerated were then transferred by the replica plating technique to the YS medium (comprising 0.2% yeast extract, 1.0% starch, 2.0% agar, pH 7.0) which further contained 20 μg/ml of streptomycin. The streptomycin resistance clones were selected from the incubated colonies. According to the above-described method for extraction of DNA, the above-mentioned various kinds of the reconstructed plasmids were extracted from the SM resistance clones as selected by the above procedure. From amongst the various kinds of the plasmids so reconstructed and selected was chosen such a recombinant plasmid which was constructed by inserting into the Bgl II-Sph I cleavage site of the vector pIJ 702 the DNA fragment which was obtained by deleting both the Sph I(1)-Sph I(2) region and the Sph I(3)-Bgl II(2) region from the 7.0 kb DNA fragments as shown on the restriction endonuclease map of FIG. 1 [i.e., such DNA fragment as obtained when the Bgl II(1)-Sph I(1) region present in the 7.0 kb DNA fragment of FIG. 1 was connected to the Sph I(2)-Sph I(3) region (which corresponded to the DNA segment of this invention having the length of about 3.8 kb) present in the 7.0 kb DNA fragment of FIG. 1]. This recombinant plasmid so chosen was named plasmid "pHT000". The plasmid pHT000 is a novel recombinant DNA molecule.

(b) One microgram of the above plasmid pHT000 was then digested (cleaved) completely with the restriction endonuclease Bgl II, followed by partial digestion (cleavage) with a small amount of the restriction endonuclease Bam HI. The resultant digestion mixture of the DNA fragments so produced were separated into the individual fragments, by electrophoresis in low melting-point agarose gel. A gel band which was containing such DNA fragment having a length of 7.9 kb (including the vector moiety) was then cut out and melted so that said DNA fragment was extracted. This fragment was cyclized with aid of the T4-DNA ligase in the same manner as described above so as to reconstruct plasmids. Thereafter, these reconstructed plasmids were used to transform protoplasts of Streptomyces lividans 66, and the streptomycin resistance clones were then selected from the resulting transformed clones. Plasmids were then extracted from the SM resistance clones thus obtained. Plasmid which was cutted out from the plasmid pHT000 but was containing such DNA fragment which was obtained by deleting both the Bgl II(1)-Bam HI(3) region and Sph I(3)-Bgl II(2) region from the 7.0 kb DNA fragment of FIG. 1 [namely, such DNA fragment which was corresponding to the Bam HI(3)-Sph I(3) region present in the DNA fragment of FIG. 1]was selected, and it was named plasmid "pHT008".

(c) On the other hand, 1 μg of the plasmid pIJ 702 described above and 1 μg of plasmid pST 141 were separately digested completely with the restriction endonuclease Sph I, followed separately by complete digestion with the restriction endonuclease Pst I. The resulting digestion mixtures were combined together and added with the T4-DNA ligase, followed by effecting the ligation reaction overnight at 4° C. The resulting mixture of the ligated DNAs was used to transform protoplasts of Streptomyces lividans 66. The resulting protoplast transformants were cultured and regenerated at 28° C. for 3 days in the R2YE medium. Plasmids were extracted from the regenerated clones. The cleavage pattern of the extracted plasmid with restriction endonucleases was investigated by electrophoresis in agarose gel. Through this investigation, there was selected such a clone which retained a plasmid containing therein a DNA fragment, which was obtained by deleting both the Bgl II(1)-Sph I(2) region and the Pst I-Bgl II(2) region from the 7.0 kb DNA fragment of FIG. 1 [namely, such DNA fragment which was corresponding to the Sph I(2)-Bam HI(3) region present in the DNA fragment of FIG. 1]. This plasmid was named "pHT002".

(d) From the plasmid pHT000 as obtained by the above procedure, was cut out a fragment which was corresponding to the Bam HI(3)-Sph I(3) region present in the 7.0 kb fragment as shown in the map of FIG. 1, and this fragment was extracted by electrophoresis on low melting-point agarose gel. This fragment was then inserted between the Bgl II cleavage site and the Sph I cleavage site of the plasmid pHT002, to prepare a plasmid. This plasmid was named "pHT010".

Experimental Example 2

In this Example, control of the expression of the streptomycin resistance gene was investigated as follows:

Strains of Streptomyces lividans which were obtained from the above Experimental Example 1 and which contained the plasmid pHT000, plasmid pHT002, plasmid pHT008 and plasmid pHT010, respectively, were separately cultured to the later stage of their logarithmic growth at 28° C. in 500-ml Erlemeyer flasks each containing 100 ml of the YEME medium therein. The cells as cultured in each of the flasks were divided in to two equal halves, and one half of the cells was transferred into a 500-ml Erlemeyer flask which contained 50 ml of the YEME medium including 5 μg/ml of streptomycin, and the other half was transferred into a 500-ml Erlemeyer flask which contained 50 ml of the streptomycin-free YEME medium. These cells were incubated overnight at 28° C. From the incubated cells in each flask was prepared a cell extract solution by a method as described hereinafter. Specific activity level (μmol/mg-protein/hour) of the streptomycin-inactivating enzyme which was present in the respective cell extract solutions was measured by a method as described hereinafter. Results as shown in the following Table 1 were thus obtained.

TABLE 1

| Plasmid retained by each strain of Streptomyces lividans | Specific enzyme activity for the cells incubated in the presence of streptomycin added | Specific enzyme activity for the cells incubated in the absence of streptomycin |
| --- | --- | --- |
| pHT000 | 11 | <1 |
| pHT002 | <1 | <1 |
| pHT008 | 9 | 6 |
| pHT010 | 6 | <1 |

In addition, the plasmids were separately extracted from the respective microbial strains and were investigated. Each plasmid was not found to vary in its quantity (that is, to involve neither increase nor decrease in the number of copies of the plasmid), depending on the presence or absence of streptomycin added.

A conclusion was hence reached, that the differences in the degree of the expression of the streptomycin resistance gene were not invoked due to the differences in the quantity of the gene-containing plasmids but were attributable directly to the presence or absence of streptomycin added. It is also apparent from the results of Table 1 that when the DNA segment which is indicated by the Bam HI(3)-Sph I(3) region present in the 7.0 kb DNA fragment of FIG. 1 is present only and singly (namely, for the case of the plasmid pHT008), the expression of the streptomycin resistance gene takes place but cannot be controlled ("on" or "off") by the addition of or the omission of streptomycin. In other words, it has been confirmed that the Bam HI(3)-Sph I(3) region which is present in the DNA fragment of FIG. 1 is indispensable for effecting the expression of the streptomycin resistance gene and that not only the DNA region (pHT002) which is indicated by the Sph I(2)-Pst I region present in the DNA fragment of FIG. 1, but also the DNA segment (pHT008) which is indicated by the Bam HI(3)-Sph I(3) region present in the DNA fragment of FIG. 1 are essential in order to control ("on" or "off") the expression of the SM resistance gene by external addition of streptomycin.

Incidentally, the measurement of the streptomycin-inactivating enzyme in the above experiment was conducted in the following manner.

Namely, each of the strains was cultured in the presence or absence of streptomycin, followed by collection of the incubated cells by centrifugation. The cells collected were washed once with the same volume of physiological saline. The cells were then suspended in a buffer solution (comprising 10 mM Tris-HCl (pH 7.6), 10 mM MgCl$_2$, 50 mM NH$_4$Cl and 3 mM 2-mercaptoethanol) to a ratio of the cells to buffer solution of 1:4, followed by disruption of the cells by sonification while being cooled in ice water. The disrupted cell homoginate was centrifuged at 2° C. and 16,000 rpm for 30 minutes in a cooled centrifugator to remove the residual cells, and to obtain a cell extract solution.

The whole proteins present in the cell extract solution were quantitatively measured in terms of the variation in the light absorbance at 595 nm as invoked by Coomassie brilliant blue, using bovin serum albumin as a standard [Bradford, "Anal. Biochem." 72, 248 (1976)]. A 5 μl or 25 μl portion of the cell extract solution, 40μl or 20 μl of sterilized water and 5μl of a buffer solution [comprising 1 M Tris-maleate (pH 7.0), 100 mM MgSO₄, 30 mM ATP and 10 mM streptomycin] were mixed together, and the resultant liquid mixture was incubated at 37° C. for 1 hour. Immediately after the reaction, the temperature was raised to 95° C., at which the mixture was then maintained for 5 minutes to inactivate the enzyme. The reaction mixture was subjected to bioassay with *Bacillus subtilis* ATCC 6633, to determine the quantity of the unreacted streptomycin which remained in the reaction mixture. The specific enzyme activity of the streptomycin-inactivating enzyme was expressed in terms of the amount of streptomycin which was decreased per mg of the protein and per hour.

Industrial Utility of the Invention

As has been described above, the DNA segment of this invention is useful vector, especially for constructing such hybrid plasmid which acts reliably as a selected marker of the streptomycin resistance, by incorporating it into a suitable plasmid vector, and the DNA segment of this invention is hence suitable for use in the gene manipulation techniques for actinomycetes of industrial use.

We claim:

1. A DNA segment containing a streptomycin resistance gene and a function to control the expression of the gene, said DNA segment consisting essentially of an SpH I-Sph I DNA segment having a length of about 3.8 kb which is obtained by excising a Bgl II-Bgl II fragment with a restriction endonuclease Sph I, said Bgl II-Bgl II fragment having been obtained by excising a hybrid plasmid pST 141 with a restriction endonuclease Bgl II, said Bgl II-Bgl II fragment having been derived from the DNA of *Streptomyces griseus* and containing the streptomycin resistance gene therein and having the restriction endonuclease site, shown in the restriction endonuclease map of FIG. 1 of the accompanying drawings and a length of 7.0 kg; and said hybride plasmid pST 141 having been constructed by ligating a Bgl II fragment of the DNA of a plasmid pIJ 702 with such a Bgl II fragment of length of 7.0 kb which is obtained by excising with the restriction endonuclease Bgl II the chromosome DNA containing the streptomycin resistance gene of *Streptomyces griseus;* and said hybrid plasmid pST 14 also having the restriction endonuclease cleaving sites shown in the restriction endonuclease map of FIG. 2 of the accompanying drawings and having a length of about 12.6 kb, said DNA segment consisting essentially of such DNA segment having a length of about 3.8 kb and containing internally the streptomycin resistance gene and a DNA region possessing the function to control the expression of the streptomycin resistance gene.

2. A DNA segment as claimed in claim 1, wherein said DNA segment is a DNA segment present in a DNA base (nucleotide) sequence according to the diagram shown in FIG. 3 of the accompanying drawings; and this DNA segment having the nucleotide sequence which is ranging from a DNA region corresponding to a Sph I cleavage site indicated by letters Sph I(3) given thereabove, to another DNA region corresponding to another Sph I cleavage site indicated by letters Sph I(2) given thereabove as shown in FIG. 3 of the accompanying drawings.

* * * * *